(12) United States Patent
Zheng et al.

(10) Patent No.: US 12,703,845 B2
(45) Date of Patent: Aug. 11, 2026

(54) AUTOMATIC DISINFECTION MACHINE FOR PLANT TISSUE CULTURE EXPLANTS

(71) Applicant: Nanjing Institute of Environmental Sciences, MEE, Nanjing (CN)

(72) Inventors: Xiao Zheng, Nanjing (CN); Yaping Hu, Nanjing (CN); Xiaomin Ge, Nanjing (CN); Hui Ding, Nanjing (CN); Shuifei Chen, Nanjing (CN); Xu Zhou, Nanjing (CN)

(73) Assignee: NANJING INSTITUTE OF ENVIRONMENTAL SCIENCES, MEE, Nanjing (CN)

( * ) Notice: Subject to any disclaimer, the term of this patent is extended or adjusted under 35 U.S.C. 154(b) by 483 days.

(21) Appl. No.: 18/471,053

(22) Filed: Sep. 20, 2023

(65) Prior Publication Data

US 2024/0400966 A1 Dec. 5, 2024

(30) Foreign Application Priority Data

Jun. 1, 2023 (CN) ......................... 202310644707.5

(51) Int. Cl.
*C12M 1/00* (2006.01)
*C12M 1/12* (2006.01)
*C12M 1/36* (2006.01)
*C12M 3/00* (2006.01)

(52) U.S. Cl.
CPC ............ *C12M 37/00* (2013.01); *C12M 41/48* (2013.01)

(58) Field of Classification Search
CPC ............. A61L 2/18; A01H 4/00; C12M 37/00
See application file for complete search history.

(56) References Cited

U.S. PATENT DOCUMENTS 10,342,191 B2 * 7/2019 Scanlon ............... A01G 25/167
2024/0251725 A1 * 8/2024 Kang ..................... A01G 31/00

FOREIGN PATENT DOCUMENTS

CN 104106466 A 10/2014
CN 206005441 U * 3/2017
CN 206658761 U 11/2017
(Continued)

OTHER PUBLICATIONS

English translation of CN 206005441 to Huang, Quan (generated 2026).*

*Primary Examiner* — Nathan A Bowers
(74) *Attorney, Agent, or Firm* — Muncy, Geissler, Olds & Lowe, P.C.

(57) ABSTRACT

An automatic disinfection machine for plant tissue culture explants, comprising a water tank, a disinfection basket, solution bottles, pumps and a valve, wherein the solution bottles are arranged in multiple and respectively filled with disinfectants and sterile water, on the water tank are provided a water inlet and a water outlet, the disinfection basket is detachably placed inside the water tank to hold plant tissues, each of the solution bottles is connected to the water inlet through one of the pumps, and the valve is provided at the water outlet and is opened at a specified time after the pumps are started. In the present invention, a controller is arranged to open the pumps and the valve, so to infuse disinfectants or sterile water into the water tank, as well as automatically discharge disinfectants or sterile water from the water tank, thereby performing disinfection and rinsing automatically without manual operation.

9 Claims, 11 Drawing Sheets

(56) References Cited

FOREIGN PATENT DOCUMENTS

CN 213044634 U * 4/2021
CN 214289721 U * 9/2021
CN 215031549 U * 12/2021
CN 215940764 U * 3/2022

* cited by examiner

AUTOMATIC DISINFECTION MACHINE FOR PLANT TISSUE CULTURE EXPLANTS

TECHNICAL FIELD

The present invention relates to the field of plant tissue disinfection equipment, in particular to an automatic disinfection machine for plant tissue culture explants.

BACKGROUND TECHNOLOGY

Subject matter disclosed in the present invention relates to disinfection of plant tissue culture explants, and related technologies have been published in following documents:

Chinese Patent Publication No. CN104106466A entitled "method for disinfecting explants in plant tissue cultures"; and Chinese Patent Publication No. CN206658761U entitled "plant tissue culture explant disinfection device".

On surfaces of explants are covered a large number of microorganisms, so strict disinfection is required before inoculation and cultivation. Usually, explants are placed in a culture bottle or a triangular flask for disinfection. The disinfection process starts with rinsing the explants with tap water, followed by rapid disinfection with 75% alcohol, after that, the explants are rinsed multiple times with sterile water, then the explants are subjected to long-term disinfection using 0.1% mercuric chloride solution or 10% sodium hypochlorite solution, shaking and agitating for a plurality of times, and finally the explants are rinsed multiple times with sterile water.

The mentioned method is primarily done manually and has following several drawbacks: firstly, the process itself and the preparation of materials are quite cumbersome, secondly, when solutions are poured, explants are liable to be washed away along with solutions, resulting in loss of research material; and lastly, as it takes time to conduct manual handling, explants need to be immersed in insufficiently poured sterile water for a long period before inoculation, resulting in a longer immersion time of explants, which will easily lead to browning during later stages of cultivation.

SUMMARY OF THE INVENTION

The present invention provides an automatic disinfection machine for plant tissue culture explants, so as to address issues encountered during manual processes of using bottles for containment, rinsing, and disinfecting explants, the explants are liable to be washed away with solutions and when being immersed in the solution the explants may brown.

In order to solve the technical problems mentioned above, the present invention offers following technical solutions:

An automatic disinfection machine for plant tissue culture explants comprises a water tank, a disinfection basket, solution bottles, pumps and a valve, wherein the solution bottles are arranged to be more than one and at least respectively filled with disinfectants and sterile water; on the water tank are provided a water inlet and a water outlet, the disinfection basket is detachably placed inside the water tank, and the disinfection basket is used to hold plant tissues; each of the solution bottles is connected to the water inlet through one of the pumps, and the pumps are used for transferring disinfectants or sterile water inside the solution bottles into the water tank so as to soak or rinse plant tissues inside the disinfection basket; and the valve is provided at the water outlet and is opened at a specified time after the pumps are started, so as to discharge the disinfectants or sterile water inside the water tank.

Further, the automatic disinfection machine for plant tissue culture explants comprises a collection bottle, wherein the valve comprises a three-way valve, and the collection bottle is connected to a port of the water outlet through the vale, and remaining ports of the valve are connected to a drainage channel.

Further, inside the water tank are provided a first roller and a second roller, at a top portion of the water tank is arranged a water tank cover, the water tank cover is detachably connected to the water tank, on the water tank cover are provided a third roller and a motor, and the motor is used for driving the third roller to rotate; the disinfection basket is in a shape of a cylindrical bucket and able to enclose plant tissues therein while rotating, the first roller and the second roller support the disinfection basket when the disinfection basket is placed inside the water tank, and when the water tank cover is closed, top portions of the disinfection basket are pressed down by the third roller; and axes of the disinfection basket, the first roller, the second roller and the third roller are arranged parallel, an outer peripheral surface of the disinfection basket is in frictional contact with an outer peripheral surface of the third roller, and when the motor is started, the disinfection basket rotates around an axis thereof within the water tank.

Further, a cross-section of the water tank is in a pentagonal shape, a bottom wall of the water tank is horizontal and connected to the water outlet, and side walls of the water tank comprise vertical walls and inclined walls; and the vertical walls are connected to top portions of the water tank, while the inclined walls are connected to a bottom surface of the water tank, the first roller and the second roller are installed on two of the inclined walls respectively, and the water inlet is connected to one of the vertical walls.

Further, both the first roller and the second roller are connected to two of the inclined walls respectively through first bearing housings, and the third roller is connected to a bottom surface of the water tank cover through a second bearing housing.

Further, the motor is fixedly connected to the water tank cover, an output shaft of the motor is connected to an input shaft of a right-angle reducer, an output shaft of the right-angle reducer is coaxially installed with a gear, the third roller comprises a friction wheel portion and a gear portion which are coaxially connected, and the gear on the third roller meshes with the gear portion.

Further, an outer wall of the water tank is provided with a rotating shaft housing, on the rotating shaft housing are provided first rotating shafts and a second rotating shaft, on the water tank cover are provided rotating arms, on the rotating arms is provided a third rotating shaft, the first rotating shafts, the second rotating shaft and the third rotating shaft are arranged parallel, and the first rotating shafts are arranged higher than the second rotating shaft; the rotating arms are connected to the rotating shaft housing through the first rotating shafts, the second rotating shaft is connected to the third rotating shaft through a telescopic rod, and when the telescopic rod performs an extension movement, the water tank cover rotates relative to the water tank around the first rotating shafts as an axis.

Further, the disinfection basket comprises a top cover, middle plates, a bottom plate, and fasteners; the top cover is connected to the bottom plate through at least one of the middle plates, the fasteners pass through the top cover, the middle plates, and the bottom plate in sequence to fix the top cover, the middle plates, and the bottom plate as a whole, and the top cover, the middle plates, and the bottom plate are made of a mesh material to allow solutions to pass; all of the top cover, the middle plates, and the bottom plate comprise plate portions and circular ring portions, and the circular ring portions extend axially along edges of the plate portions; and the top cover and the middle plates, adjacent middle plates, the middle plates and the bottom plate are connected with the circular ring portions, so as to form flat cylindrical cleaning chambers between the top cover and the middle plates, between the adjacent middle plates, and between the middle plates and the bottom plate, and the cleaning chambers are used to hold plant tissues.

Further, an edge of the top cover forms a first annular flange which extends radially outward, an edge of the bottom plate forms a second annular flange which also extends radially outward, and an axial distance between the first annular flange and the second annular flange is greater than axial lengths of the first roller, the second roller, and the third roller.

Further, among the plate portions are uniformly provided a plurality of sleeves axially extending, two of the plurality of sleeves on adjacent coaxial plate portions are socket-connected, the fasteners comprise bolts and nuts, the bolts pass through the plurality of sleeves and are threaded with the nuts to fix the top cover, the middle plates, and the bottom plate together; and an amount of the sleeves on one of the plate portions satisfies a following condition: plant tissues have difficulties in radially moving inside the cleaning chambers.

Compared to the prior art, the present invention has following beneficial effects:

In the automatic disinfection machine for plant tissue culture explants of the present invention, a controller is arranged to open the pumps and the valve, so as to automatically infuse disinfectants or sterile water into the water tank, as well as automatically discharge disinfectants or the sterile water from the water tank, thereby performing disinfection and rinsing processes automatically without manual operation; and plant tissues are placed inside a cleaning basket, which prevents the plant tissues from being washed away when solutions are discharged.

BRIEF DESCRIPTION OF THE DRAWINGS

In order to more clearly illustrate embodiments of the present invention or the technical solutions in the prior art, in the following paragraphs accompanying drawings that are required in the description of the embodiments or the prior art will be briefly introduced. Apparently, the accompanying drawings in the following description are only exemplary, and those skilled in the art can also obtain other implementation drawings according to the provided drawings without creative work.

Figure 1:
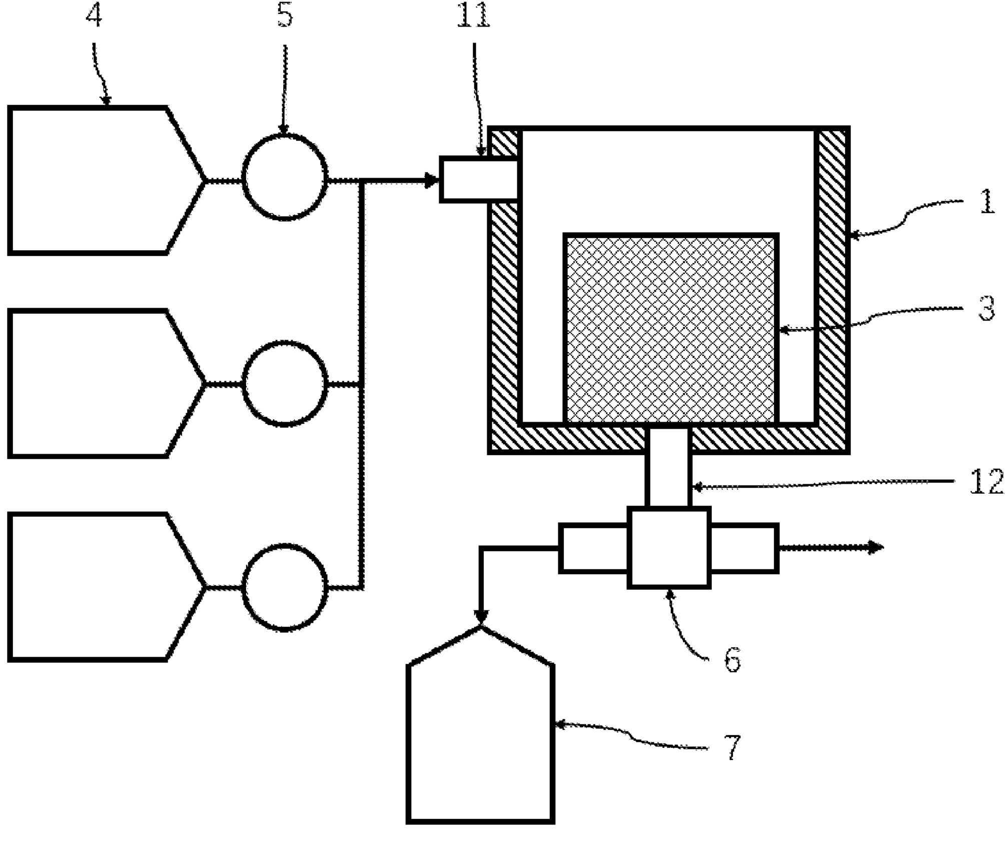
FIG. 1 is a system block of Embodiment 1 of the present invention.
Figure 2:
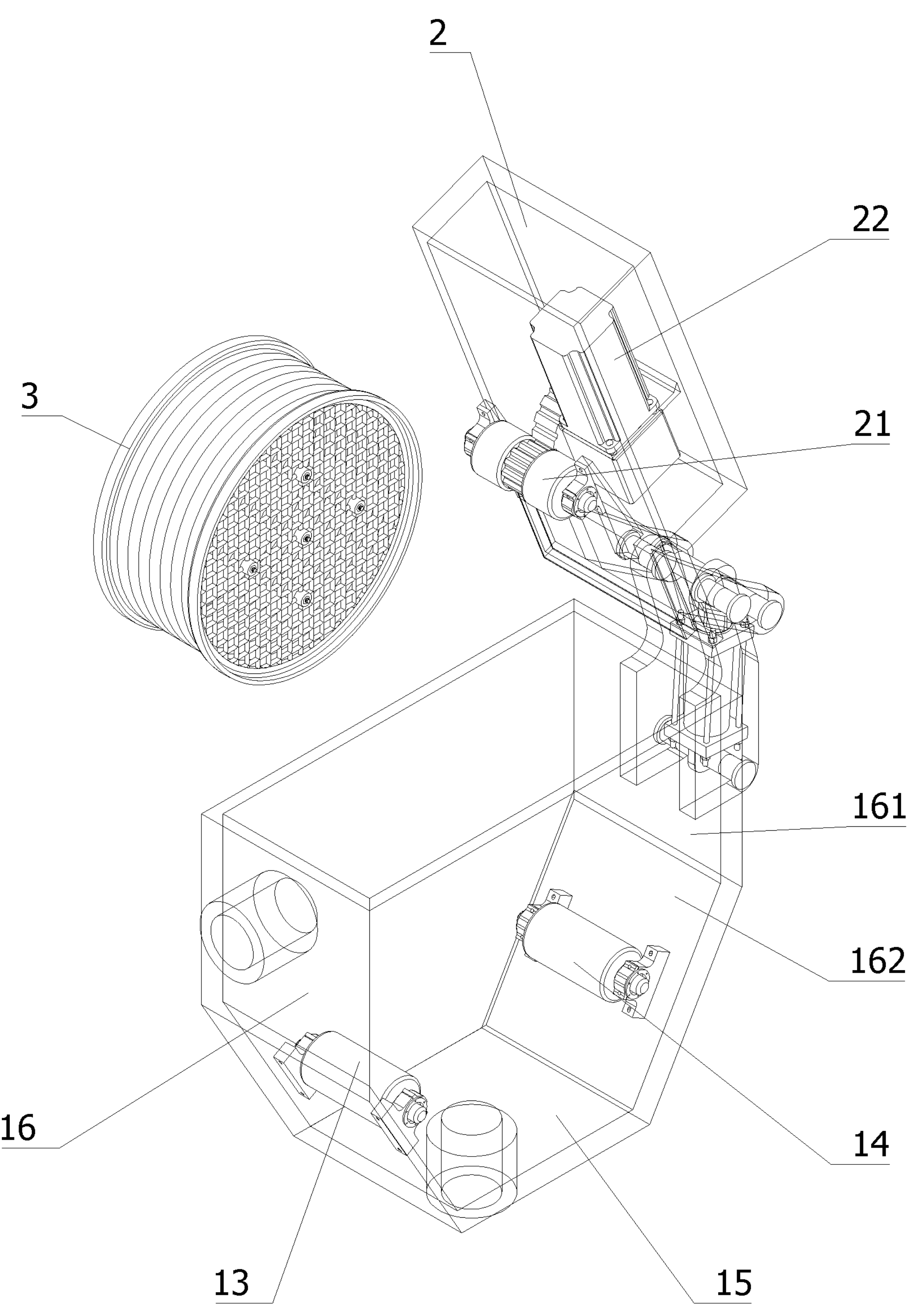
FIG. 2 is a perspective view of a water tank of Embodiment 2 of the present invention in a first working condition, wherein both the water tank and the water tank cover are in a perspective state, and the first working condition refers to that the disinfection basket is located outside the water tank and the water tank cover is opened.
Figure 3:
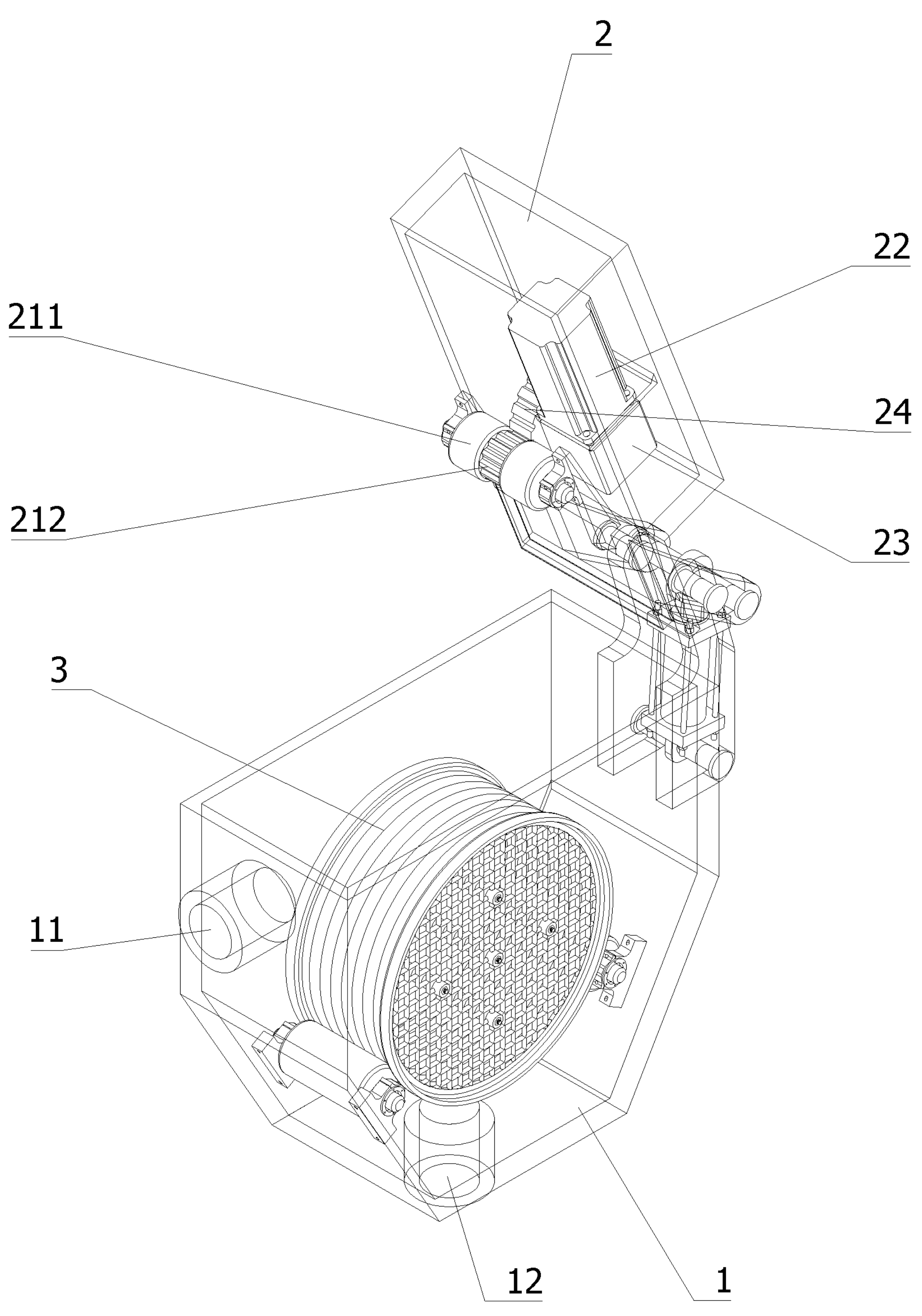
FIG. 3 is a perspective view of the water tank of Embodiment 2 of the present invention in a second working condition, wherein the second working condition refers to that the disinfection basket is located inside the water tank and the water tank cover is opened.
Figure 4:
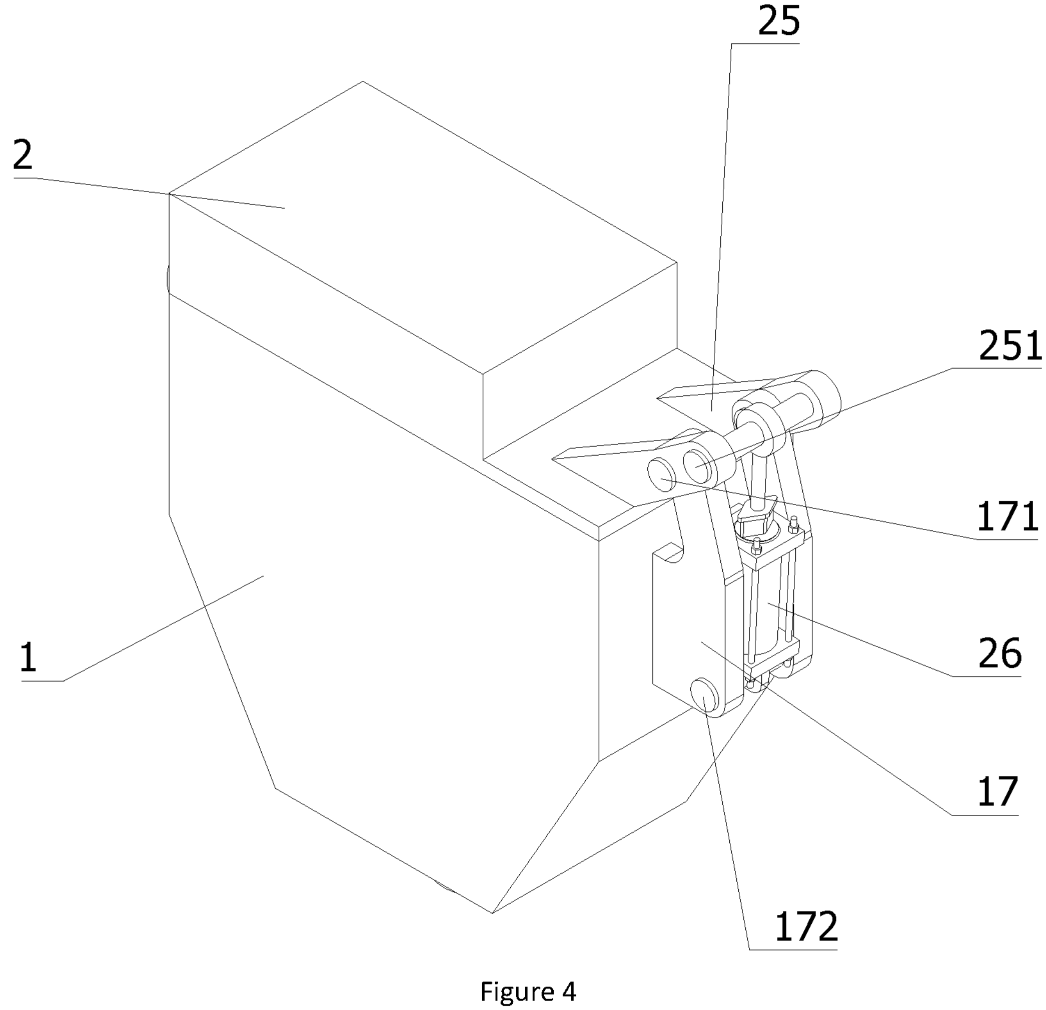
FIG. 4 is a perspective view of the water tank of Embodiment 2 of the present invention in a third working condition, wherein the third working condition refers to that the disinfection basket is located inside the water tank and the water tank cover is closed.
Figure 5:
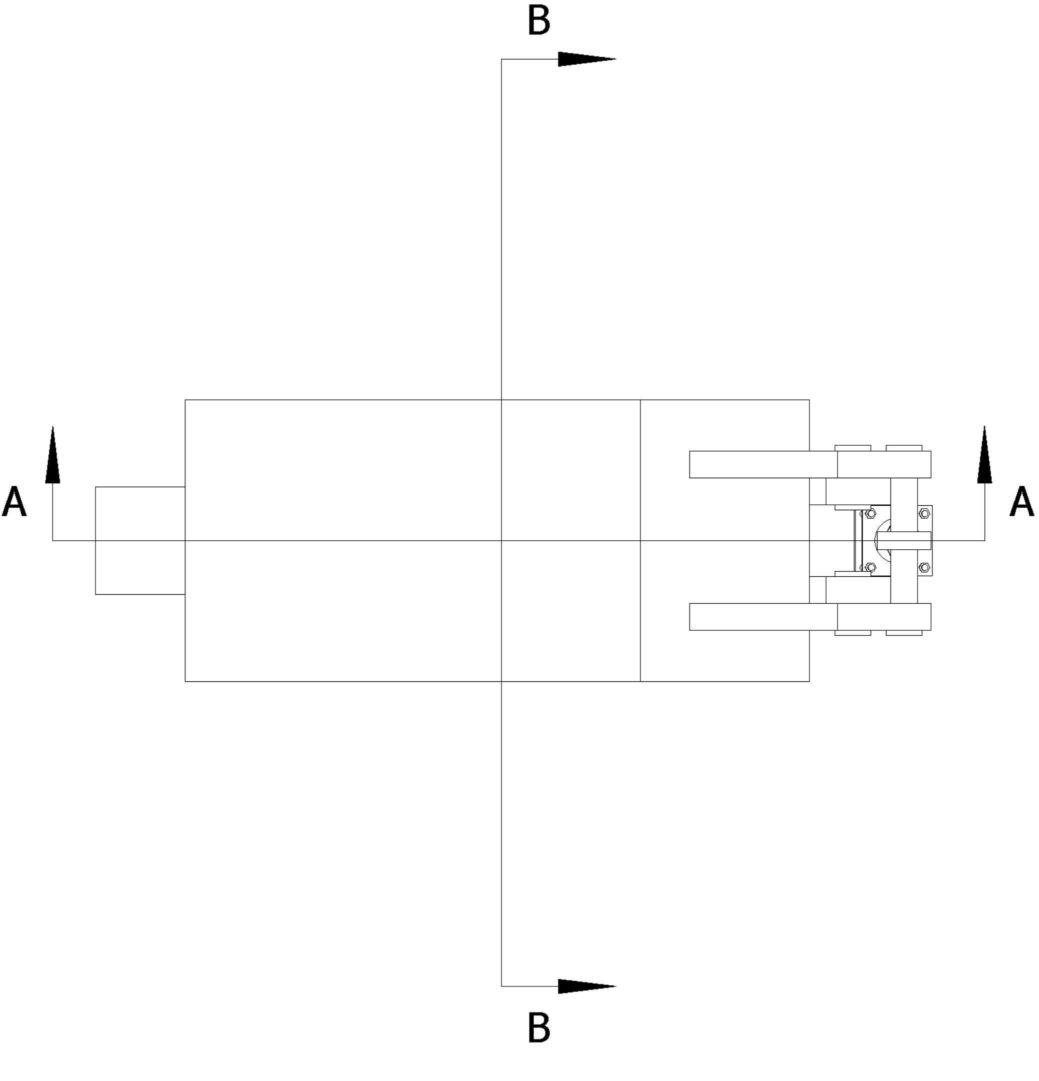
FIG. 5 is a bottom view of the water tank of Embodiment 2 of the present invention in the third working condition.

The markups in the drawings are indicated as follows:

1—water tank;
11—water inlet;
12—water outlet;
13—first roller;
14—second roller;
15—bottom wall;
16—side wall;
161—vertical wall;
162—inclined wall;
17—rotating shaft housing;
171—first rotating shaft;
172—second rotating shaft;
2—water tank cover;
21—third roller;
211—friction wheel portion;
212—gear portion;
22—motor;
23—right—angle reducer;
24—gear;
25—rotating arm;
251—third rotating shaft;
26—telescopic rod;
3—disinfection basket;
31—top cover;
311—first annular flange;
32—middle plate;
33—bottom plate;
331—second annular flange;
34—fastener;
341—bolt;
342—nut;
35—plate portion;
351—sleeve;
36—ring portion;
37—cleaning chamber;
38—annular groove;
4—solution bottle;
5—pump;
6—valve; and
7—collection bottle.

SPECIFIC EMBODIMENTS

The following paragraphs will clearly and completely describe the technical solutions in embodiments of the present invention with reference to the accompanying drawings in the embodiments of the present invention. Obviously, the described embodiments are only some embodiments of the present invention rather than all embodiments of the present invention. Based on the embodiments of the present invention, all other embodiments obtained by persons of ordinary skill in the art without making creative efforts belong to the protection scope of the present invention.

During manual processes of using bottles for containment, and rinsing and disinfecting explants, there are issues such as explants being easily washed away with solutions and the tendency of explants to undergo browning due to prolonged immersion in solutions.

In order to solve the technical problems mentioned above, an automatic disinfection machine for plant tissue culture explants is offered.

Embodiment 1 (Please See FIG. 1)

An automatic disinfection machine for plant tissue culture explants, comprising a water tank 1, a disinfection basket 3, solution bottles 4, pumps 5 and a valve 6, wherein

- the solution bottles 4 are arranged to be more than one and at least respectively filled with disinfectants and sterile water;
- on the water tank 1 are provided a water inlet 11 and a water outlet 12, the disinfection basket 3 is detachably placed inside the water tank 1, and the disinfection basket 3 is used to hold plant tissues;
- each of the solution bottles 4 is connected to the water inlet 11 through one of the pumps 5, and the pumps 5 are used for transferring disinfectants or sterile water inside the solution bottles 4 into the water tank 1 so as to soak or rinse plant tissues inside the disinfection basket 3; and
- the valve 6 is provided at the water outlet 12 and is opened at a specified time after the pumps 5 are started, so as to discharge disinfectants or sterile water inside the water tank 1.

In the Embodiment 1, there are at least three of the solution bottles, respectively containing 75% alcohol, disinfectants (0.1% mercuric chloride solution or 10% sodium hypochlorite solution), and sterile water.

The pumps 5 and the valve 6 are controlled by a controller, which is not shown in the drawings, and flushing and disinfection are conducted in accordance to following steps of:

- Step 1: adding the 75% alcohol to the water tank 1, shaking the disinfection basket 3 for 30 seconds, and then emptying the water tank 1;
- Step 2: adding sterile water to the water tank 1, shaking the disinfection basket 3 for 30 seconds, and then emptying the water tank 1;
- Step 3: adding disinfectants solution to the water tank 1, shaking the disinfection basket 3 for 10 minutes, and then emptying the water tank 1; and
- Step 4: adding sterile water to the water tank 1, shaking the disinfection basket 3 for 30 seconds, then emptying the water tank 1.

In the above steps, the step of shaking the disinfection basket 3 can be done manually or by using an oscillator. Alternatively, instead of shaking the disinfection basket 3, an ultrasonic cleaning device can be used to release ultrasound into solutions to ensure sufficient contact between solutions and plant tissues.

Furthermore, due to disinfectants are prone to polluting the environment and should not be directly discharged. To address the mentioned issue, following technical solutions are offered.

The automatic disinfection machine for plant tissue culture explants further comprises a collection bottle 7, wherein the valve 6 is a three-way valve, and the collection bottle 7 is connected to a port of the water outlet through the vale 6, and remaining ports of the valve 6 are connected to a drainage channel.

In the steps 1, 2 and 4, the 75% alcohol and sterile water are discharged directly into the drainage channel; and in the step 3, the valve 6 switches passages thereof so that the disinfectants are discharged into the collection bottle 7 for recycling purposes.

Further, in the Embodiment 1, positions of the water inlet 11 and the water outlet 12 are fixed, which means water in the water tank 11 also flows in a fixed direction, resulting in plant tissues inside the disinfection basket 3 being constantly impacted by flowing water and flushed to a corner of the disinfection basket 3, and causing the plant tissues to be piled up against each other, even when the disinfection basket 3 is shaken to disperse the plant tissues inside, it is difficult to achieve uniform distribution of the plant tissues within solutions, and uneven distribution affects effectiveness of rinsing and disinfection.

In order to solve the technical problems mentioned above, Embodiment 2 is offered (please refer to FIGS. 2~6).

Inside the water tank 1 are provided a first roller 13 and a second roller 14, at a top portion of the water tank 1 is arranged a water tank cover 2, the water tank cover 2 is detachably connected to the water tank 1, on the water tank cover 2 are provided a third roller 21 and a motor 22, and the motor 22 is used for driving the third roller 21 to rotate;

the disinfection basket 3 is in a shape of a cylindrical bucket and able to enclose plant tissues therein while rotating, the first roller 13 and the second roller 14 support the disinfection basket 3 when the disinfection basket 3 is placed inside the water tank 1, and when the water tank cover 2 is closed, top portions of the disinfection basket 3 are pressed down by the third roller 21; and

- axes of the disinfection basket 3, the first roller 13, the second roller 14 and the third roller 21 are arranged parallel to each other, an outer peripheral surface of the disinfection basket 3 is in frictional contact with an outer peripheral surface of the third roller 21, and when the motor 22 is started, the disinfection basket 3 rotates around an axis thereof within the water tank 1.

When impacted by the flowing water, the plant tissues inside the disinfection basket 3 tend to accumulate at bottom portions of the disinfection basket 3. As the disinfection basket 3 rotates, accumulated plant tissues underneath move towards top portions of the disinfection basket 3, and then suspend in the solutions and descend slowly, allowing more even distribution of the plant tissues within the solutions.

After a disinfection process is finished, the water tank cover 2 is opened so as to take the disinfection basket 3 out.

Preferably, a cross-section of the water tank 1 is in a pentagonal shape, a bottom wall 15 of the water tank 1 is horizontal and connected to the water outlet 12, and side walls 16 of the water tank 1 comprise vertical walls 161 and inclined walls 162; and the vertical walls 161 are connected to top portions of the water tank 1, while the inclined walls 162 are connected to a bottom surface of the water tank 1, the first roller 13 and the second roller 14 are installed on two of the inclined walls 162 respectively, and the water inlet 11 is connected to one of the vertical walls 161.

The inclined walls 162 are used to reduce distances between inner walls of the water tank 1 and the disinfection basket 3, thus saving amounts of both the disinfectants and the sterile water required.

Additionally, the inclined walls 162 are arranged to reduce a surface area of the bottom wall 15 of the water tank 1, which is good for speeding up drainage.

Preferably, both the first roller 13 and the second roller 14 are connected to the two of the inclined walls 162 respectively through first bearing housings, and the third roller 21 is connected to a bottom surface of the water tank cover 2 through a second bearing housing.

Preferably, the motor 22 is fixedly connected to the water tank cover 2, an output shaft of the motor 22 is connected to an input shaft of a right-angle reducer 23, an output shaft of the right-angle reducer 23 is coaxially installed with a gear 24, the third roller 21 comprises a friction wheel portion 211 and a gear portion 212 which are coaxially connected, and the gear 24 on the third roller meshes with the gear portion 212.

The right-angle reducer 23 adopts a worm gear transmission, with both the gear 24 and the gear portion 212 using straight gears, and the friction wheel portion 211 comprises two wheels, which are arranged at two ends of the gear portion 212 respectively.

Further, in the Embodiment 2, the motor 22, the right-angle reducer 23, the gear 24, and the third roller 21 are all installed on the water tank cover 2, which results in a heavy weight of the water tank cover 2, and repeatedly moving of the water tank cover 2 imposes a significant physical burden on workers.

Figure 6:
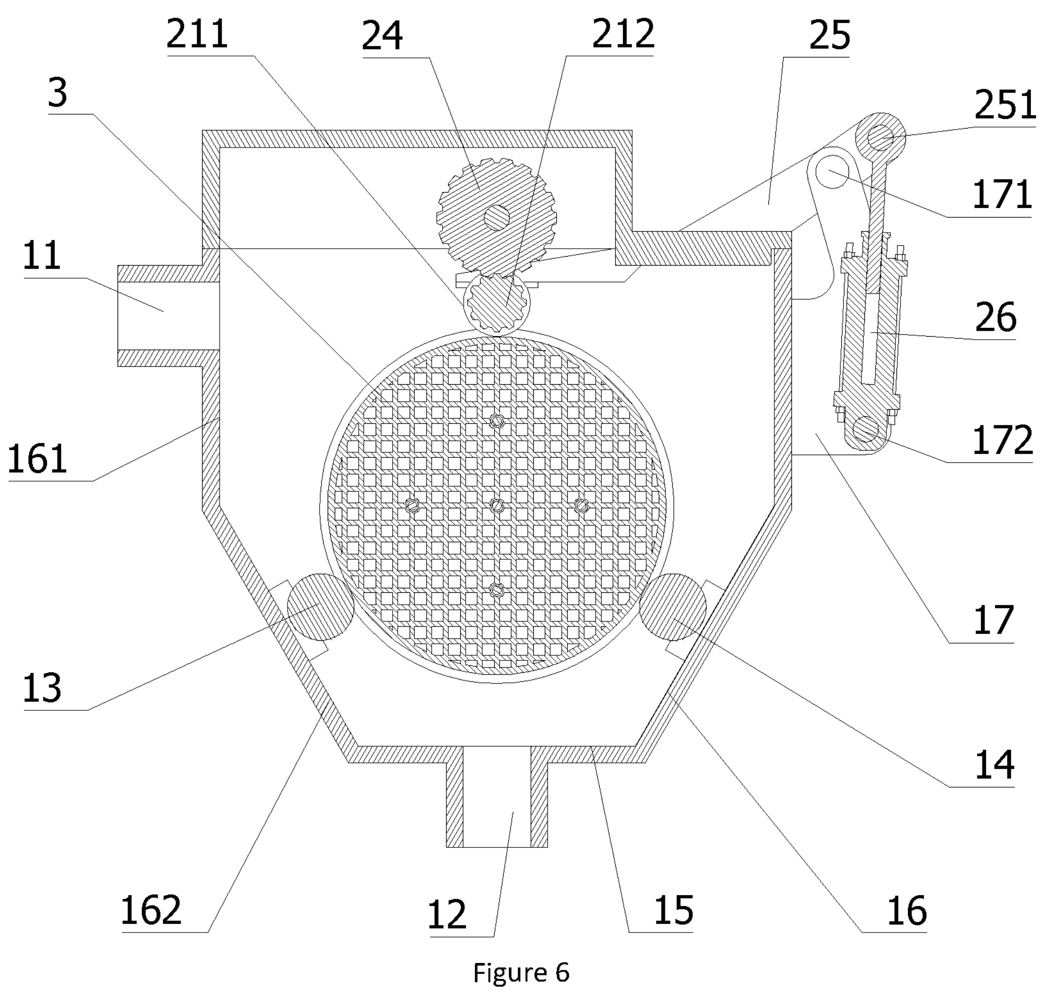
FIG. 6 is a cross-sectional view from an A-A direction of FIG. 5.
Figure 7:
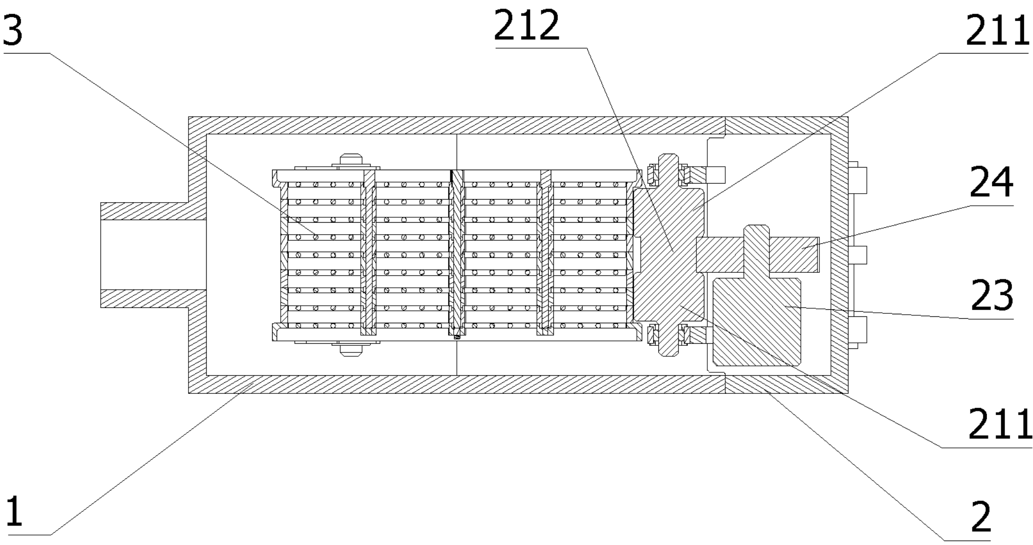
FIG. 7 is a cross-sectional view from a B-B direction of FIG. 5.
Figure 8:
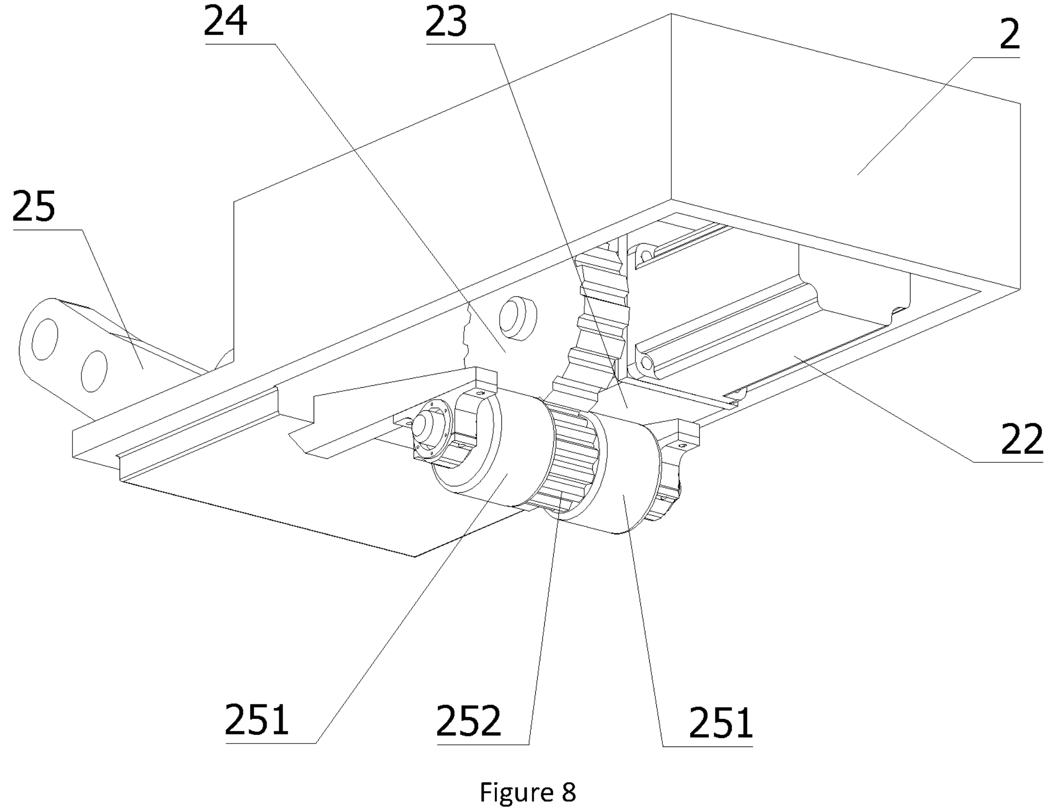
FIG. 8 is a perspective view of the water tank cover of Embodiment 2 of the present invention.
Figure 9:
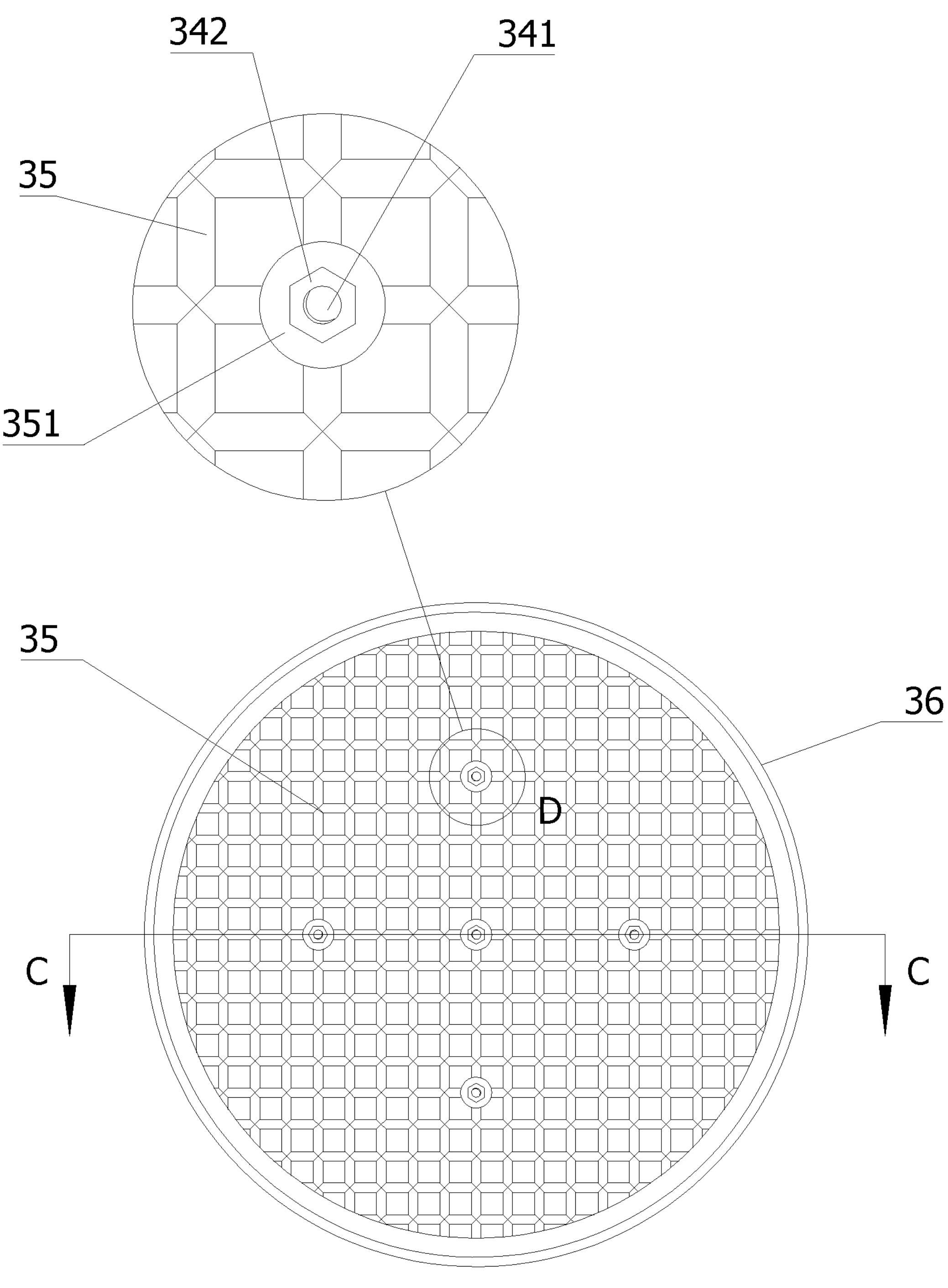
FIG. 9 is an axial view of a cleaning basket in Embodiment 2 of the present invention, and an enlarged view of a partial structure thereof.
Figure 10:
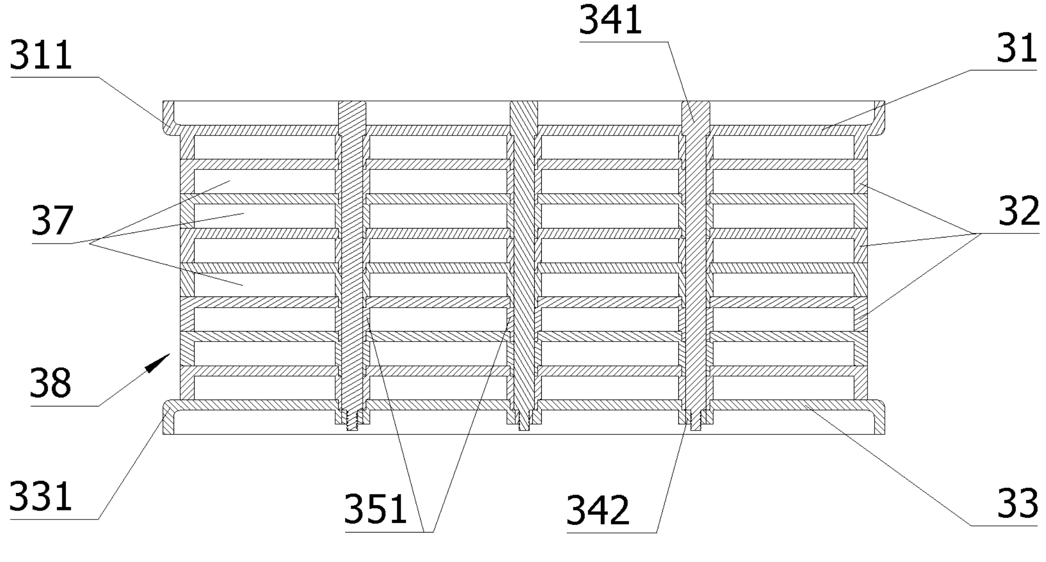
FIG. 10 is a cross-sectional view of a C-C direction of FIG. 9.
Figure 11:
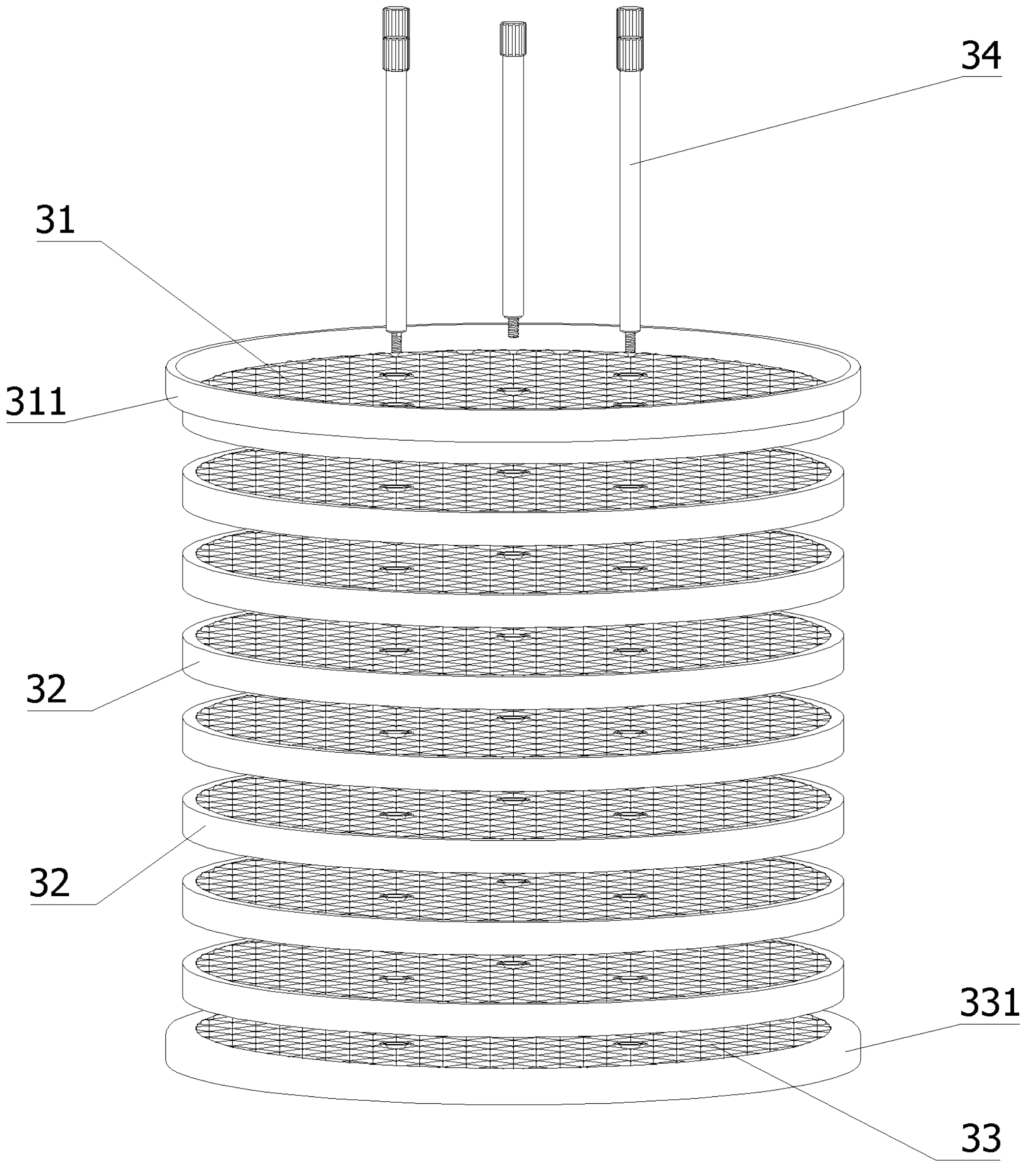
FIG. 11 is an assembly drawing of the cleaning basket of Embodiment 2 of the present invention.
Figure 12:
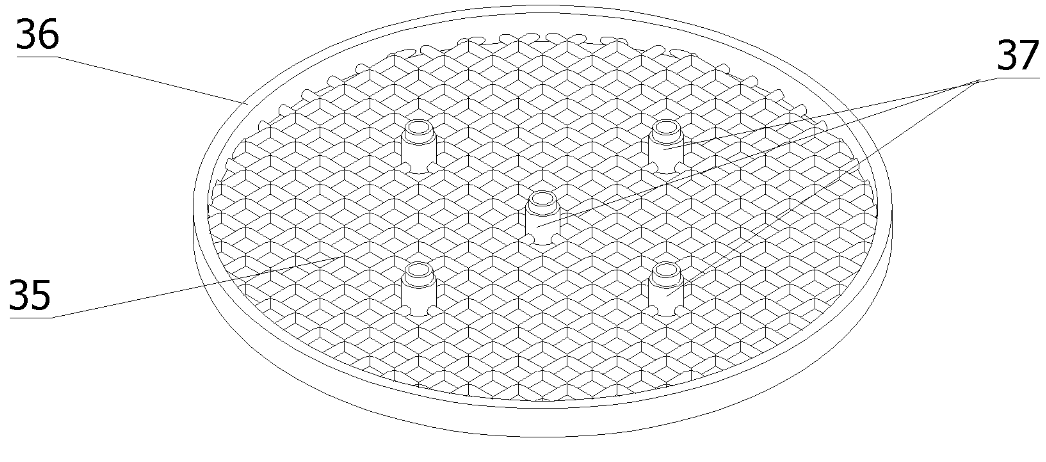
FIG. 12 is a perspective view of a middle plate of Embodiment 2 of the present invention.

In order to solve the above mentioned technical solutions, following technical solutions are offered and please see FIGS. 6~8.

An outer wall of the water tank 1 is provided with a rotating shaft housing 17, on the rotating shaft housing 17 are provided first rotating shafts 171 and a second rotating shaft 172, on the water tank cover 2 are provided rotating arms 25, on the rotating arms 25 is provided a third rotating shaft 251, the first rotating shafts 171, the second rotating shaft 172 and the third rotating shaft 251 are arranged parallel to each other, and the first rotating shafts 171 are arranged higher than the second rotating shaft 172;

the rotating arms 25 are connected to the rotating shaft housing through the first rotating shafts 171, the second rotating shaft 172 is connected to the third rotating shaft 251 through a telescopic rod 26, and when the telescopic rod 26 performs an extension movement, the water tank cover 2 rotates relative to the water tank 1 around the first rotating shafts 171 as an axis.

The telescopic rod 26 utilizes an electric servo push rod or a cylinder to achieve automatic opening and closing of the water tank cover 2, which reduces physical exertion of workers. When a cylinder is used to close the water tank cover 2, an elastic force is provided to push the third roller 21 against the outer peripheral surface of the disinfection basket 3, thereby increasing friction between the third roller 21 and the disinfection basket 3.

Further, in the Embodiment 2, some plant tissues may accumulate at the bottom portions of the disinfection basket 3 due to the impact of the flowing water, leading to mutual entanglement or tangling, and even when the disinfection basket 3 is rotated, it is difficult to disperse tangled plant tissues from each other.

In order to solve the technical problems mentioned above, following technical solutions are offered and please refer to FIG. 9~12.

the disinfection basket 3 comprises a top cover 31, middle plates 32, a bottom plate 33, and fasteners 34;

the top cover 31 is connected to the bottom plate 33 through at least one of the middle plates 32, the fasteners 34 pass through the top cover 31, the middle plates 32, and the bottom plate 33 in sequence to fix the top cover 31, the middle plates 32, and the bottom plate 33 as a whole, and the top cover 31, the middle plates 32, and the bottom plate 33 are all made of mesh material so that the disinfection basket 3 allows solutions to pass;

the top cover 31, the middle plates 32, and the bottom plate 33 all comprise plate portions 35 and circular ring portions 36, and the circular ring portions 36 extend axially along edges of the plate portions 35; and the top cover 31 and the middle plates 32, adjacent middle plates 32, the middle plates 32 and the bottom plate 33 are all connected with the circular ring portions 36, so as to form flat cylindrical cleaning chambers 37 between the top cover 31 and the middle plates 32, between the adjacent middle plates 32, and between the middle plates 32 and the bottom plate 33, and the cleaning chambers 37 are used to hold plant tissues.

A plurality of the middle plates 32 separate the disinfection basket 3 into a plurality of the cleaning chambers 37, thereby allowing the plant tissues to be separated from each other, which helps to prevent the plant tissues from entangling with each other under the impact of the flowing water.

Further, an edge of the top cover 31 forms a first annular flange 311 which extends radially outward, an edge of the bottom plate 33 forms a second annular flange 331 which also extends radially outward, the first annular flange 311, the second annular flange 331, and an outer wall of the ring section 36 form a circular groove 38, and an axial distance between the first annular flange 311 and the second annular flange 331 is greater than axial lengths of the first roller 13, the second roller 14, and the third roller 21.

The circular groove 38 engages with the first roller 13, the second roller 14, and the third roller 21, restricting an axial movement of the disinfection basket 3, which prevents the disinfection basket 3 from disengaging from a working area formed by the first roller 13, the second roller 14, and the third roller 21 during rotation.

Further, among the plate portions 35 are uniformly provided a plurality of sleeves 351 axially extending, two of the plurality of sleeves 351 on adjacent plate portions 35 that are coaxial with each other are socket-connected, the fasteners 34 comprise bolts 341 and nuts 342, the bolts 341 pass through the plurality of sleeves 351 and are threaded with the nuts 342 to fix the top cover 31, the middle plates 32, and the bottom plate 33 as a whole; and an amount of the sleeves 351 on a same plate portion 35 satisfies a following condition: plant tissues have difficulties in radially moving inside the cleaning chambers 37.

In the present invention, workers can bypass the sleeves 351 to place plant tissues on the plate portions 35, and then stack the middle plates 32 layer by layer; and after the disinfection basket 3 is assembled, the sleeves 351 act as interposing pillars inside the cleaning chambers 37, so that when the disinfection basket 3 rotates, the plant tissues inside a same cleaning chamber 37 have difficulties in coming into contact with each other.

For ease of operation, the nuts 342 are fixed to the bottom plate 33 with adhesive, and head portions of the bolts 341 are equipped with knobs.

The above embodiments are merely illustrative examples of the present invention and should not be considered as limiting protection scope of the present invention. The protection scope of the present invention is defined by the claims. Those skilled in the art can make various modifications or equivalent substitutions within the substance and protection scope of the present invention, which should also be considered within the protection scope of the embodiments of the present invention.

The invention claimed is:

1. An automatic disinfection machine for plant tissue culture explants, comprising a water tank, a disinfection basket, solution bottles, pumps and a valve, wherein the solution bottles are arranged to be more than one and respectively filled with at least disinfectants and sterile water;

on the water tank are provided a water inlet and a water outlet, the disinfection basket is detachably placed inside the water tank, and the disinfection basket is used to hold plant tissues;

each of the solution bottles is connected to the water inlet through one of the pumps, and the pumps are used for transferring disinfectants or sterile water inside the solution bottles into the water tank so as to soak or rinse plant tissues inside the disinfection basket; and the valve is provided at the water outlet and is opened at a specified time after the pumps are started, so as to discharge disinfectants or sterile water inside the water tank;

wherein inside the water tank are provided a first roller and a second roller, at a top portion of the water tank is arranged a water tank cover, the water tank cover is detachably connected to the water tank, on the water tank cover are provided a third roller and a motor, and the motor is used for driving the third roller to rotate;

the disinfection basket is in a shape of a cylindrical bucket and able to enclose plant tissues therein while rotating, the first roller and the second roller support the disinfection basket when the disinfection basket is placed inside the water tank, and when the water tank cover is closed, top portions of the disinfection basket are pressed down by the third roller; and axes of the disinfection basket, the first roller, the second roller and the third roller are arranged parallel, an outer peripheral surface of the disinfection basket is in frictional contact with an outer peripheral surface of the third roller, and when the motor is started, the disinfection basket rotates around an axis thereof within the water tank.

2. The automatic disinfection machine for plant tissue culture explants according to claim 1, further comprising a collection bottle, wherein the valve comprises a three-way valve, and the collection bottle is connected to a port of the water outlet through the vale, and remaining ports of the valve are connected to a drainage channel.

3. The automatic disinfection machine for plant tissue culture explants according to claim 1, wherein a cross-section of the water tank is in a pentagonal shape, a bottom wall of the water tank is horizontal and connected to the water outlet, and side walls of the water tank comprise vertical walls and inclined walls; and the vertical walls are connected to top portions of the water tank, while the inclined walls are connected to a bottom surface of the water tank, the first roller and the second roller are installed on two of the inclined walls respectively, and the water inlet is connected to one of the vertical walls.

4. The automatic disinfection machine for plant tissue culture explants according to claim 3, wherein both the first roller and the second roller are connected to the two of the inclined walls respectively through first bearing housings, and the third roller is connected to a bottom surface of the water tank cover through a second bearing housing.

5. The automatic disinfection machine for plant tissue culture explants according to claim 1, wherein the motor is fixedly connected to the water tank cover, an output shaft of the motor is connected to an input shaft of a right-angle reducer, an output shaft of the right-angle reducer is coaxially installed with a gear, the third roller comprises a friction wheel portion and a gear portion which are coaxially connected, and the gear on the third roller meshes with the gear portion.

6. The automatic disinfection machine for plant tissue culture explants according to claim 1, wherein an outer wall of the water tank is provided with a rotating shaft housing, on the rotating shaft housing are provided at least one first rotating shaft and a second rotating shaft, on the water tank cover are provided rotating arms, on the rotating arms is provided a third rotating shaft, the at least one first rotating shaft, the second rotating shaft and the third rotating shaft are arranged parallel, and the first rotating shafts are arranged higher than the second rotating shaft;

the rotating arms are connected to the rotating shaft housing through the at least one first rotating shaft, the second rotating shaft is connected to the third rotating shaft through a telescopic rod, and when the telescopic rod performs an extension movement, the water tank cover rotates relative to the water tank around the at least one first rotating shaft as an axis.

7. The automatic disinfection machine for plant tissue culture explants according to claim 1, wherein the disinfection basket comprises a top cover, middle plates, a bottom plate, and fasteners;

the top cover is connected to the bottom plate through at least one of the middle plates, the fasteners pass through the top cover, the middle plates, and the bottom plate in sequence to fix the top cover, the middle plates, and the bottom plate as a whole, and the top cover, the middle plates, and the bottom plate are all made of mesh material to allow solutions to pass;

the top cover, the middle plates, and the bottom plate comprise plate portions and circular ring portions, and the circular ring portions extend axially along edges of the plate portions; and the top cover and the middle plates, adjacent middle plates, the middle plates and the bottom plate are all connected with the circular ring portions, so as to form flat cylindrical cleaning chambers between the top cover and the middle plates, between the adjacent middle plates, and between the middle plates and the bottom plate, and the cleaning chambers are used to hold plant tissues.

8. The automatic disinfection machine for plant tissue culture explants according to claim 7, wherein an edge of the top cover forms a first annular flange which extends radially outward, an edge of the bottom plate forms a second annular flange which also extends radially outward, and an axial distance between the first annular flange and the second annular flange is greater than axial lengths of the first roller, the second roller, and the third roller.

9. The automatic disinfection machine for plant tissue culture explants according to claim 7, wherein among the plate portions are uniformly provided a plurality of sleeves axially extending, two of the plurality of sleeves on adjacent plate portions that are coaxial are socket-connected, the fasteners comprise bolts and nuts, the bolts pass through the plurality of sleeves and are threaded with the nuts to fix the top cover, the middle plates, and the bottom plate; and an amount of the sleeves on a same plate portion satisfies a following condition: plant tissues have difficulties in radially moving inside the cleaning chambers.

* * * * *